United States Patent [19]

D'Amico

[11] 4,149,871
[45] Apr. 17, 1979

[54] ALKYLTHIOALKYL ESTERS OF 2-OXO-3-BENZOTHIAZOLINEACETIC ACID AS PLANT GROWTH REGULATORS

[75] Inventor: John J. D'Amico, Olivette, Mo.
[73] Assignee: Monsanto Company, St. Louis, Mo.
[21] Appl. No.: 861,478
[22] Filed: Dec. 16, 1977
[51] Int. Cl.$^2$ ............................................. A01N 9/12
[52] U.S. Cl. ................................... 71/90; 260/304 B
[58] Field of Search ............................ 260/304; 71/90
[56] References Cited
U.S. PATENT DOCUMENTS
3,069,429  12/1962  Goodson et al. ................... 260/304

OTHER PUBLICATIONS

L. G. Nickell, "Plant Growth Regulators", Chem. & Eng. News, Oct. 9, 1978, pp. 18–34.

*Primary Examiner*—Donald G. Daus
*Assistant Examiner*—D. B. Springer
*Attorney, Agent, or Firm*—Richard H. Shear; Donald W. Peterson

[57] ABSTRACT

Alkylthioalkyl esters of 2-oxo-3-benzothiazolineacetic acid have been found to be effective in regulating the growth of leguminous plants.

4 Claims, No Drawings

ALKYLTHIOALKYL ESTERS OF 2-OXO-3-BENZOTHIAZOLINEACETIC ACID AS PLANT GROWTH REGULATORS

This invention relates to certain alkylthioalkyl esters of 2-oxo-3-benzothiazolineacetic acid. More specifically, the invention relates to such esters having the formula

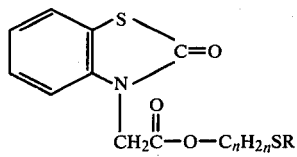

wherein R is alkyl, preferably having from one to five carbon atoms, inclusive and n is an integer from one to five, inclusive. The esters of the foregoing formula have been found to be effective in regulating the growth of leguminous plants, especially soybean.

Leguminous plants have canopies that effectively inhibit sunlight from reaching the lower leaves. For example, only about 50% of a soybean plant's leaves intercept light for photosynthesis. Approximately 85% of the light is absorbed by the outer layer of leaves. Many researchers feel that by altering the morphology of the leaves such that the canopy is altered, light may fall more deeply into the canopy, and yields could be increased. Weber, in Field Crop Abstracts, Vol. 21, No. 4, pages 313–317, states that "greater light penetration, resulting in greater amount of the [soybean] plant canopy having a light intensity above 150 f.c., generally led to higher seed yields." Johnson et al, in Crop Science, Vol. 9, pages 577–581, states that "adding light increased the yields of bottom, middle and top canopy positions of [soybean] plants 30, 20 and 2%, respectively." Thus, it would be highly beneficial if a method was found whereby the canopy of such plants could be altered such that a greater number of leaves could be illuminated.

The term "plant regulant" or "plant growth regulant", as employed in this application, connotes a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, such as an increase or decrease in dry weight accumulation, stature reduction, leaf or canopy alteration, increased branching, terminal inhibition, increased flowering or fruit set.

Modifications in the normal sequential development of a treated plant to agricultural maturity may also be manifested by reduced transpiration or increased carbohydrate deposition or protein content.

It is to be understood that the regulation of plants in accordance with the instant invention does not include the total inhibition or the killing of such plants. Although phytotoxic amounts of the materials disclosed herein might be employed to exert a herbicidal (killing) action, it is contemplated herein to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amount will vary, not only with the material selected, but also with the modifying effect desired, the species of plant and its stage of development, the plant growth medium and whether a permanent or transitory effect is sought.

It is presently known that certain benzothiazyl compounds possess herbicidal activity. U.S. Pat. No. 3,069,429 discloses the use of derivatives of 4-halogeno-2-oxobenzothiazolin-3-ylacetic acid to kill weeds. U.S. Pat. No. 3,651,074 and 3,839,349 disclose the use of certain 2-oxo-3-benzothiazolines as a herbicide. None of these patents, however, disclose the use of the specific benzothiazolines used in accordance with the present invention to regulate the growth of plants. Further, none of these patents disclose the use of such benzothiazolines to alter the canopy of leguminous plants.

It is further known that certain benzothiazyl compounds possess plant growth regulating activity. U.S. Pat. No. 2,468,075 discloses the use of such compounds as abscission agents. Japanese Pat. No. 71/21378 discloses that such compounds possess plant growth regulating activity, but does not disclose any specific uses. Japanese Pat. No. 73/10182 discloses the use of benzothiazyl compounds as grafting agents for tree root growth. U.S. Pat. No. 3,661,921 discloses 2-oxo-3-benzothiazolineacetamides as anti-inflammatory agents. U.S. Pat. No. 4,049,419 discloses the use of certain 2-oxo-3-benzothiazolineacetic acid derivatives as plant growth regulants.

The prior art does not disclose, however, the esters of 2-oxo-3-benzothiazolineacetic acid of the foregoing formula nor does the prior art disclose the use of those esters as a plant growth regulant for leguminous plants.

The esters of the foregoing formula may be prepared in accordance with the following scheme:

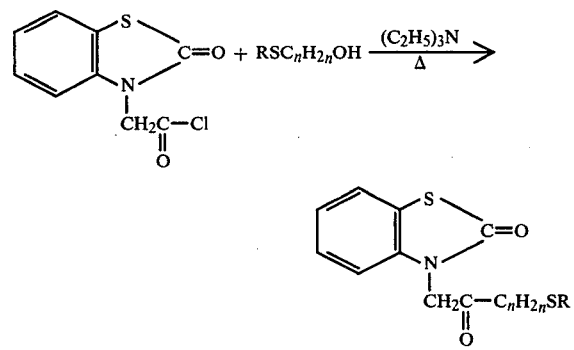

Perferably, n is two.

As an illustration of the preparation of the compounds of the invention, [2-(methylthio)ethyl] 2-oxo-3- benzothiazolineacetate and [2-(butylthio)ethyl] 2-oxo-3-benzothiazolineacetate have been prepared as follows:

To a stirred solution containing 22.8 grams (0.1 mole) of 2-oxo-3-benzothiazolineacetyl chloride, 150 ml of tetrahydrofuran and 0.1 mole of 2-hydroxyethyl methyl sulfide or 2-hydroxyethyl butyl sulfide, 11.3 grams (0.11 mole) of triethylamine is added in one portion. An exothermic reaction set in causing a temperature rise from 24° to 53° C. The stirred reaction mixture is heated at reflux for 24 hours. After cooling to 25° C., 800 grams is added and stirring continued at 0°–10° C. for one hour. The solid is collected by filtration, washed with cold water until the washings are neutral to litmus and air-dried at 25°–30° C. The data are summarized in Table I.

Table I

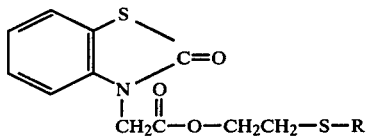

| R | m.p.° C. | Percent Yield | Percent C Calc'd. | Percent C Found | Percent H Calc'd. | Percent H Found | Percent N Calc'd. | Percent N Found | Percent S Calc'd. | Percent S Found |
| --- | --- | --- | --- | --- | --- | --- | --- | --- | --- | --- |
| —CH$_3$ | 43-4[a] | 44 | 50.86 | 51.00 | 4.62 | 4.65 | 4.94 | 4.96 | 22.63 | 22.52 |
| —C$_4$H$_9$ | 57-8[a] | 35 | 55.36 | 55.47 | 5.88 | 5.89 | 4.30 | 4.33 | 19.70 | 19.67 |

[a] Recrystallization from heptane.

In accordance with the novel aspects of the present invention, the esters of 2-oxo-3-benzothiazolineacetic acid of the foregoing formula are used as the active ingredient in compositions that are useful as plant growth regulants. In practicing the plant growth regulating methods of this invention, the active ingredient can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent, or emulsifying agent or any suitable combination of these.

When applying the active ingredient to leguminous plants, useful finely-divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful in applying the active ingredient to leguminous plants include, for example, Stoddard solvent, acetone, alcohols, glycols, ethyl acetate, benzene and the like. Such leguminous plant growth regulating compositions, particularly liquids and wettable powders, usually contain as a conditioning agent one or more surface-active agents in amounts sufficient to render a given composition readily dispersible in water or in oil. By the term "surface-active agent", it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts active ingredient, about 1 to 50 parts surface-active agent and about 4 to 94 parts solvent, all parts being by weight based on the total weight of the composition.

Desirable modification of leguminous plants may be achieved by applying the above-described plant regulants to the plant locus. The term "plant locus" is understood herein to include the plant growing medium, such as the soil, as well as the seeds, emerging seedlings, roots, stems, leaves, flowers, fruits or other plant parts.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. If desired, application of the compositions of the invention to leguminous plants can be accomplished by incorporating the compositions in the soil or other media in the area where modification of the plants is desired.

To illustrate the variety of regulatory responses observed, the compounds of the invention were tested in accordance with the following procedure.

A number of soybean plants are grown from seeds in plastic pots in the greenhouse for a period of one week at which time the plants are thinned to one plant per pot. When the second trifoliate leaf is fully expanded, the plants are treated with a solution of the active ingredient in acetone and water. Aqueous Tween 20 is used as a surfactant.

When the fifth trifoliate leaf of the control is fully expanded, the treated plants are compared with the non-treated control plants and the observations recorded.

The following observations were made when soybeans were treated at the indicated rates with [2-(methylthio)ethyl] 2-oxo-3-benzothiazolineacetate.

| Rate (kg/h) | Observations |
| --- | --- |
| 2.8 | Stature reduction, epinasty, leaf alteration, leaf inhibition, altered canopy, decreased dry weight accumulation, slight leaf burn. |
| 0.56 | Stature reduction, epinasty, leaf alteration, leaf inhibition, altered canopy, decreased dry weight accumulation. |
| 0.112 | Stature reduction, stem distortion, leaf alteration, leaf inhibition, altered canopy, decreased dry weight accumulation. |

The following observations were made when soybeans were treated at the indicated rates with [2-(butylthio)ethyl] 2-oxo-3-benzothiazolineacetate.

| Rate (kg/h) | Observations |
| --- | --- |
| 2.8 | Stature reduction, epinasty, leaf alteration, leaf inhibition, altered canopy, decreased dry weight accumulation, slight leaf burn. |
| 0.56 | Stature reduction, stem distortion, leaf alteration, leaf inhibition, altered canopy, decreased dry weight accumulation. |
| 0.112 | Stature reduction, stem distortion, leaf alteration, leaf inhibition, altered canopy, decreased dry weight accumulation. |

In selecting the appropriate non-toxic rate of application of the active ingredient to leguminous plants, it will be recognized that precise rates will also be dependent upon the mode of application, such as soil incorporation, band application, pre-plant seed treatment, result desired and various other factors known to those skilled in the art. In applications to the soil habitat of germinant seeds, emerging seedlings, and established vegetation for the regulation of plant growth, the active ingredients are applied in amounts of from about 0.05 to about 20 pounds per acre or more (0.056 to 22.4 kilos/hectare). Foliar application is particularly advantageous and is preferred especially from about 0.1 to about 5.0 pounds per acre (0.112 to about 5.6 kilos/hectare).

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of regulating the growth of leguminous plants which comprises applying to the plant locus a plant growth regulating effective amount of a compound having the formula

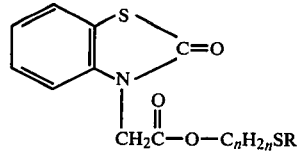

wherein R is alkyl having from one to five carbon atoms, inclusive and n is an integer from one to five, inclusive.

2. A method according to claim 1 wherein n is two.

3. A method according to claim 2 which is [2-(methylthio)ethyl] 2-oxo-3-benzothiazolineacetate.

4. A method according to claim 2 which is [2-(butylthio)ethyl] 2-oxo-3-benzothiazolineacetate.

* * * * *